US008263136B2

(12) United States Patent
Caswell

(10) Patent No.: US 8,263,136 B2
(45) Date of Patent: Sep. 11, 2012

(54) LOW DOSE COLONIC CLEANSING SYSTEM

(75) Inventor: Michael L. Caswell, Lynchburg, VA (US)

(73) Assignee: C.B. Fleet Company Inc., Lynchburg, VA (US)

( * ) Notice: Subject to any disclaimer, the term of this patent is extended or adjusted under 35 U.S.C. 154(b) by 0 days.

(21) Appl. No.: 13/208,812

(22) Filed: Aug. 12, 2011

(65) Prior Publication Data

US 2011/0308988 A1    Dec. 22, 2011

Related U.S. Application Data

(62) Division of application No. 11/839,474, filed on Aug. 15, 2007, now Pat. No. 7,998,510.

(60) Provisional application No. 60/822,703, filed on Aug. 17, 2006.

(51) Int. Cl.

| A61K 33/42 | (2006.01) |
|---|---|
| A61K 33/06 | (2006.01) |
| A61K 33/08 | (2006.01) |
| A61K 33/14 | (2006.01) |
| A61P 1/00 | (2006.01) |
| A61K 31/70 | (2006.01) |

(52) U.S. Cl. ............... 424/606; 424/78.01; 424/601
(58) Field of Classification Search .................. None
See application file for complete search history.

(56) References Cited

U.S. PATENT DOCUMENTS

| H859 H | 12/1990 | Augustine |
|---|---|---|
| 5,013,716 A | 5/1991 | Cherukuri et al. |
| 5,106,632 A | 4/1992 | Wong et al. |
| 5,124,144 A | 6/1992 | Giorgetti et al. |
| 5,274,001 A | 12/1993 | Borody |
| 5,498,425 A | 3/1996 | Wood et al. |
| 5,616,346 A | 4/1997 | Aronchick |
| 5,688,529 A | 11/1997 | Lidgate et al. |
| 5,997,906 A | 12/1999 | Wood et al. |
| 6,103,268 A | 8/2000 | Borody et al. |
| 6,156,332 A | 12/2000 | Bakal et al. |
| 6,162,464 A | 12/2000 | Jacob et al. |
| 6,361,799 B1 | 3/2002 | Palkhiwala |
| 6,737,068 B2 | 5/2004 | Durden |
| 6,806,256 B2 | 10/2004 | Ulrich et al. |
| 6,866,873 B2 | 3/2005 | Stern |
| 6,906,038 B2 | 6/2005 | Mazer |
| 6,946,149 B2 | 9/2005 | Cleveland |
| 7,101,572 B2 | 9/2006 | Santos et al. |
| 7,169,381 B2 | 1/2007 | Barras et al. |
| 7,332,184 B2 | 2/2008 | Vanner et al. |
| 7,867,521 B2 | 1/2011 | Ayala et al. |
| 7,985,429 B2 | 7/2011 | Caswell |
| 7,998,510 B2 | 8/2011 | Caswell |
| 8,129,430 B2 | 3/2012 | Caswell et al. |
| 2002/0137803 A1 | 9/2002 | Kirkland |
| 2004/0071779 A1 | 4/2004 | Keiser et al. |
| 2004/0101491 A1 | 5/2004 | Stier |
| 2004/0115282 A1 | 6/2004 | Keiser et al. |
| 2004/0143005 A1* | 7/2004 | Barras et al. .................. 514/474 |
| 2004/0170698 A1 | 9/2004 | Halow |
| 2004/0192614 A1* | 9/2004 | Vanner et al. .................. 514/23 |
| 2005/0061861 A1 | 3/2005 | Pennino |
| 2005/0271749 A1 | 12/2005 | Borody et al. |
| 2006/0051428 A1 | 3/2006 | Ayala et al. |
| 2007/0082061 A1 | 4/2007 | Ayala et al. |
| 2007/0207216 A1 | 9/2007 | Caswell |
| 2008/0145445 A1 | 6/2008 | Ayala et al. |
| 2011/0274765 A1 | 11/2011 | Caswell |

FOREIGN PATENT DOCUMENTS

| BE | 541665 | 8/1959 |
|---|---|---|
| EP | 0396165 | 11/1990 |
| WO | WO 88/03762 | 6/1988 |
| WO | WO89/05659 | 6/1989 |
| WO | WO 93/17589 | 9/1993 |
| WO | WO 94/12191 | 6/1994 |
| WO | WO 98/26776 | 6/1998 |
| WO | WO 98/43654 | 10/1998 |
| WO | WO 2004/032926 | 4/2004 |
| WO | WO 2004/037292 | 5/2004 |
| WO | WO 2006/028632 | 3/2006 |
| WO | WO 2006/118562 | 11/2006 |
| WO | WO 2007/022435 | 2/2007 |
| WO | WO 2007/044681 | 4/2007 |

OTHER PUBLICATIONS

Balaban et al.; "Comparison of Two Dosing Regimens of Liquid Sodium Phosphate Against a Low Dose PEG Regimen," Nature Publishing Group, American Journal of Gastroenterology, vol. 100, No. 9—Supplement, Sep. 2005, pp. S354-S355.*
Food and Drug Administration: "Guidance for Industry: Container Closure Systems for Packaging Human Drugs and Biologics," United States Department of Health and Human Services, May 1999, pp. 1-56.*
Rex et al.; "Updated recommendations on the safe and effective use of oral sodium phosphate solution," retrieved from <www.fleetlabs.com/notices/UpdatedRecommendationsOSPS.pdf> on Jan. 13, 2012, dated Feb. 4, 2007, pp. 1-10.* DiPalma et al.; "Biochemical Effects of Oral Sodium Phosphate," 1996, Plenum Publishing Co., Digestive Disorders and Sciences, vol. 41, No. 4, pp. 749-753.*
Ainley et al.; "Measurement of Serum Electrolytes and Phosphate After Sodium Phosphate Colonoscopy Bowel Preparation an Evaluation," 2005, Springer, Digestive Diseases and Sciences, vol. 50, No. 7, pp. 1319-1323.*
Malik, Pramod; Balaban, David H.; Thompson, William O.; and Galt, Deborah J. B.; "Randomized Study Comparing Two Regimens of Oral Sodium Phosphates Solution Versus Low-Dose Polyethylene Glycol and Bisacodyl," Springer, Digestive Diseases and Sciences, vol. 54, No. 4, pp. 833-841, (published online Aug. 19, 2008).*
Verghese, V.J. et al., "Low-salt Bowel Cleansing Preparation (LoSo Prep) as Preparation for Colonoscopy: A Pilot Study", Aliment Pharmacol Ther, vol. 16, pp. 1327-1331, (2002).
Reddy, D. et al., "Efficacy and Safety of Oral Sodium Phosphate Versus Polyethylene Glycol Solution for Bowel Preparation for Colonoscopy", Indian Journal of Gastroenterology, vol. 21, pp. 219-221, (2002).
Martinek, J. et al., "Preparation of the Gut Before Colonoscopy", Prakt., vol. 82, pp. 472-476, (2002). (original and translated version).
Web Page: Wild Resolver, Obtained from: www.wild.de/wild/opencms/en/innovation/technology/wild_innovation_technology_resolver.html, p. 1, Printed: Aug. 20, 2004.

(Continued)

Primary Examiner — David J Blanchard
Assistant Examiner — Ivan Greene
(74) Attorney, Agent, or Firm — Evan Law Group LLC

(57) ABSTRACT

A method of colonic cleansing that includes administering orally a first dose and a second dose of a liquid osmotic colonic evacuant composition. The second dose includes an amount of the liquid osmotic colonic evacuant composition that is 55% to 95% of the amount of the first dose.

18 Claims, 1 Drawing Sheet

OTHER PUBLICATIONS

Web Page: Crystal Light Product Information, Obtained from: www.kraftfoods.com/crystallight/cl_products.html, pp. 1-2, Printed: Feb. 17, 2004.
Web Page: Kraft Food Products, Pink Lemonade, Obtained from: www.kraftfoods.com/knet_print_version.aspx?s=product&m=product/product_display&Product=4300095019&print_show=1&U3=4300095019, p. 1, Printed: May 19, 2004.
Web Page: Kraft Food Products, Lemonade, Obtained from: www.kraftfoods.com/knet_print_version.aspx?s=product&m=product/product_display&Product=4300095023&print_show=1&U3=4300095023, p. 1, Printed: May 19, 2004.
Web Page: Kraft Food Products, Sunrise Classic Orange, Obtained from: www.kraftfoods.com/knet_print_version.aspx?s=product&m=product/product_display&Product=4300094541&U3=4300094541, p. 1, Printed: May 18, 2004.
Web Page: Kraft Food Products,Tangerine Strawberry, Obtained from: www.kraftfoods.com/knet_print_version.aspx?s=product&m=product/product_display&Product=4300095024&U3=4300095024, p. 1, Printed: May 19, 2004.
Web Page: Kraft Food Products, Rasberry Ice, Obtained from: www.kraftfoods.com/knet_print_version.aspx?s=product&m=product/product_display&Product=4300095028&print_show=1&U3=4300095028, p. 1, Printed: May 19, 2004.
Web Page: Kraft Food Products, Rasberry Peach, Obtained from: www.kraftfoods.com/knet_print_version.aspx?s=product&m=product/product_display&Product=4300095026&print_show=1&U3=4300095026, page 1, Printed: May 19, 2004.
Anonymous, "Product Information—Crystal Light Iced Tea Decaffeinated Sugar Free"., http://www.kraftfoods.com/main.aspx?s=product&m=product/Product_display&Site=1&Product=4300095016, p. 1, Printed: Dec. 2, 2005.
Anonymous, "Product Information—Jell-O Gelatin Dessert Orange 0 carb Sugar Free 10.2g"., hrrp://www.greatlowcarb.com/product.php?p=4085?w=100>.,pp. 1-2, Printed: Dec. 2, 2005.
International Search Report and Written Opinion dated Jan. 11, 2006 for corresponding PCT application No. PCT/US2005/028132.
Web Page: Crystal Light-Lemonade-Pink Lemonade Sugar Free Product Information, Obtained from: http://www.kraftfoods.com/knet_print_version.aspx?s=product&m=product/product_display& Product=4300095019&print_show=1, 1 page, printed Apr. 30, 2007.
Web Page: Crystal Light-Lemonade-Raspberry Lemonade Sugar Free Product Information, Obtained from: http://www.kraftfoods.com/knet_print_version.aspx?s=product&m=product/product_display&Product=4300094963&print_show=1, 1 page, printed Apr. 30, 2007.
Web Page: Crystal Light-Fruit Drinks-Strawberry-Kiwi Sugar Free Product Information, Obtained from: http://www.kraftfoods.com/knet_print_version.aspx?s=product&m=product/product_display& Product=4300095008&print_show=1, 1 page, printed Apr. 30, 2007.
Web Page: Crystal Light-Fruit Drinks-Strawberry-Orange-Banana Sugar Free Product Information, Obtained from: http://www.kraftfoods.com/knet_print_version.aspx?s=product&m=product/product_display&Product=4300095009&print_show=1, 1 page, printed Apr. 30, 2007.
Web Page: Crystal Light-Fruit Drinks-Pineapple-Orange Sugar Free Product Information, Obtained from: http://www.kraftfoods.com/knet_print_version.aspx?s=product&m=product/product_display& Product=4300095022&print_show=1, 1 page, printed Apr. 30, 2007.
Web Page: Crystal Light-Sunrise-Sunrise Ruby Red Grapefruit Product Information, Obtained from: http://www.kraftfoods.com/knet_print_version.aspx?s=product&m=product/product_display& Product=4300097199&print_show=1, 1 page, printed Apr. 30, 2007.
Anal itching [online] retrieved on Nov. 5, 2006; retrieved from the internet [http://www.cnn.com/HEALTH/library/DS/00453.html]; pp. 1-4, May 5, 2006.
Met-Rx Berry Drink Data sheet online [retrieved Mar. 21, 2002] http://www.physicallyelite.com/store/store.cfm?do=detail&product_id=12384, pp. 1-5.
Ingredient list for EAS Myoplex original nutrition shake. Retrieved from: web.archive.org/web/20001110133600 and www.eas.com/index.asp on Apr. 6, 2006. Myoplex datasheet online [retrieved Nov. 10, 2000] http://eas.com/index.asp, Myoplex pp. 1-2.
Rao, "Toxicologic Pathology of the Kidney and Urinary Bladder," Toxicologic Pathology, vol. 30, No. 6, pp. 651-656, 2002.
Vanner et al., "A Randomized Prospective Trial Comparing Oral Sodium Phosphate with Standard Polyethylene Glycol-Based Lavage Solution (Golytely) in the Preparation of Patients for Colonoscopy," The American Journal of Gastroenterology, vol. 85, No. 4, pp. 422-427, 1990.
Toblli et al., "Potassium citrate administration ameliorates tubulointerstitial lesions in rats with uric acid nephropathy," Clinical Nephrology, vol. 55, No. 1, pp. 59-68, 2001.
Lacour et al., "Effet du citrate et des phosphate sur le transport du calcium dans l'iléon de rat in vitro," Gastroenterol Clin. Biol., 18, pp. 938-944, 1994. (Summary in English).
Oikawa et al., "Modulation of plasminogen activator inhibitor-1 in vivo : A new mechanism for the anti-fibrotic effect of rennin-angiotensin inhibition," Kidney International, vol. 51, pp. 164-172, 1997.
Marangella et al., "Crystallization Inhibitors in the Pathophysiology and Treatment of Nephrolithiasis," Urologia Int., 72, Suppl. 1, pp. 6-10, 2004.
Neuhofer et al., "Chronic COX-2 inhibition reduces medullary HSP70 expression and induces papillary apoptosis in dehydrated rats," Kidney International, vol. 65, pp. 431-441, 2004.
Ma et al., "Model of robust induction of glomerulosclerosis in mice: Importance of genetic background," Kidney International, vol. 64, pp. 350-355, 2003.
Smoyer et al., "Ischemic Acute Renal Failure Induces Differential Expression of Small Heat Shock Proteins," J Am Soc Nephrol, 11, pp. 211-221, 2000.
Desmeules et al., "Acute Phosphate Nephropathy and Renal Failure," NEJM, 349, pp. 1006-1007, 2003.
Markowitz et al., "Acute Phosphate Nephropathy following Oral Sodium Phosphate Bowel Purgative: An Underrecognized Cause of Chronic Renal Failure," J Am Soc Nephrol, 16, pp. 3389-3396, 2005.
Markowitz et al., "Renal Failure Due to Acute Nephrocalcinosis Following Oral Sodium Phosphate Bowel Cleansing," Human Pathology, 35, 675-684, 13 pages total, 2004.
Ritskes-Hoitinga et al., "Phosphorus-Induced Nephrocalcinosis and Kidney Function in Female Rats," J. Nutr., 119, pp. 1423-1431, 1989.
Orias et al., "Extreme Hyperphosphatemia and Acute Renal Failure after a Phosphorus-Containing Bowel Regimen," Am J Nephrol, 19, pp. 60-63, (1999).
Fine et al., "Severe Hyperphosphatemia Following Phosphate Administration for Bowel Preparation in Patients With Renal Failure: Two Cases and a Review of the Literature," American Journal of Kidney Diseases, vol. 29, No. 1, pp. 103-105, (1997).
Wangoo et al., "Chronobiology of urinary citrate excretion amongst stone-fomers and healthy males from North Western India", Urological Research, 19:203-206, (1991).
Moeckel et al, "Distribution of de novo synthesized betaine in rat kidney: role of renal synthesis on medullary betaine accumulation," Am. J. Physiol., 272, pp. F94-F99, (1997).
Moeckel et al, "COX2 Activity Promotes Organic Osmolyte Accumulation and Adaptation of Renal Medullary Interstitial Cells to Hypertonic Stress," Journal of Biological Chemistry, vol. 278, No. 21, pp. 19352-19357, (2003).
Moeckel et al., "Role of integrin $\alpha_1\beta_1$ in the regulation of renal medullary osmolyte concentration," Am J Physiol Renal Physiol, 290, pp. F223-F231, (2006).
Marshall et al., "Prospective, randomized trial comparing sodium phosphate solution with polyethylene glycol-electrolyte electrolyte lavage for colonoscopy preparation," Gastrointestinal Endoscopy, vol. 39, No. 5, pp. 631-634, (1993).
Petsite.com Ltd., "Amazing Rodent Facts," located at http://www.petalia.com.auftemplates/StoryTemplate_Process.cfm?Story_No=350, p. 1, printed Nov. 2007.
Nie et al., "Distinct Contributions of T1R2 and T1R3 Taste Receptor Subunits to the Detection of Sweet Stimuli," Current Biology, vol. 15, pp. 1948-1952, (2005).

International Food Information Council Foundation, "Everything You Need to Know About Sucralose," 2 pages, (1998).
International Food Information Council Foundation, "Everything You Need to Know About Acesulfame Potassium," 2 pages, (1998).
Calorie Control Council, "Low-Calorie Sweeteners: Acesulfame Potassium," can be found at http://www.caloriecontrol.org/acesluf.html, 3 pages, (2004).
International Food Information Council Foundation, "Low-Calorie Sweeteners:Adding Reduced-Calorie Delights to a Healthful Diet," can be found at http://www.ific.org/foodinsight/1998/jf/lcsfi198.cfm?renderforprint=1, 4 pages, (1998).
International Food Information Council Foundation, "More Choices for the Sweet Life," can be found at http://www.ific.org/foodinsight/2002/so/morechoicesfi502.cfm?renderforprint=1, 3 pages, (2002).
FoodProductionDaily.com/Europe, "Sweet taste study promises perfect sugar replacement," can be found at http://www.foodproductiondaily.com/news/printNewsBis.asp?id=63743, 2 pages, (2005).
International Search Report dated Mar. 29, 2007 for application No. PCT/US2006/039419.
Khashab, M. et al., "Efficacy and tolerability of a new formulation of sodium phosphate tablets (INKP-101), and a reduced sodium phosphate dose, in colon cleansing: a single-center open-label pilot trial", Aliment Pharmacol Ther., vol. 21, pp. 465-468, (2005).
Rex, D.K. et al., "Safety and efficacy of two reduced dosing regimens of sodium phosphate tablets for preparation prior to colonoscopy", Aliment Pharmacol Ther., vol. 16, pp. 937-944, (2002).
Salix Pharmaceuticals, Inc., "Visicol® Product Information", http://www.salix.com/products_visicol.aspx, 1 page, printed on Aug. 16, 2006.
InKine Pharmaceutical Company, Inc., "INKP-102 Tablet Posters; A new purgative from InKine Pharmaceutical Company, Inc., a subsidiary of Salix Pharmaceuticals", American College of Gastroenterology, Annual Scientific Meeting, 28 pages, Oct. 30-Nov. 2, 2005.
Gatorade Sports Science Institute, "Roundtable; Intestinal fluid absorption in exercise and disease", SSE Roundtable #11, found at http://gssiweb.com/Article_Detail.aspx?articleid=50&level=4 topic=5, vol. 4, No. 1, 5 pages, (1993), (2002).
McNaught, A.D. "Nomenclature of carbohydrates; recommendations 1996", Pure & Applied Chemistry, vol. 68, No. 10, pp. 1919-2008, (1996).
Gatorade Beverage Comparison Chart, http://www.gssiweb.com/pdf/gatorade_bev_chart.pdf#search=%22gatorade%20beverage%20comparison%20chart%22, 2 pages, printed Sep. 2005.
Sports Drink Comparisons, The University of Arizona, Group 14, Honors Biology 181, Fall 1998, found at http://student.biology.arizona.edu/honors98/group14/sportsdrinks.html, 2 pages, printed on Feb. 25, 2008.
Accelerade, "Sports Drink Comparison", PacificHealth Laboratories, Inc., found at http://www.accelerade.com/pages/product_compare.html, 1 page, printed on Sep. 29, 2005.
All-Sport Body Quencher, "Product Comparison", found at http://www.drinkallsport.com/pop/product_compare.htm, 1 page, printed on Sep. 29, 2005.
Afridi, S.A. et al., "Prospective, randomized trial comparing a new sodium phosphate-bisacodyl regimen with conventional PEG-ES lavage for outpatient colonoscopy preparation," Gastrointestinal Endoscopy, pp. 485-489, vol. 41, (1995).
Arezzo, A. "Prospective randomized trial comparing bowel cleaning preparations for colonoscopy," Surgical Laparoscopy: Endoscopy & Percutaneous Techniques, pp. 215-217, vol. 10, No. 4, (2000).
Aronchick, C.A. et al., "A novel tableted purgative for colonoscopic preparation: efficacy and safety comparisons with Colyte and Fleet Phospho-Soda," Gastrointestinal Endoscopy, pp. 346-352, vol. 52, No. 3, (2000).
Avery, M.E. et al., "Oral therapy for acute diarrhea: the underused simple solution," The New England Journal of Medicine, pp. 891-894, vol. 323, No. 13, (1990).
Barclay, R.L. et al., "Carbohydrate-electrolyte rehydration protects against intravascular volume contraction during colonic cleansing with orally administered sodium phosphate", Gastrointestinal Endoscopy, pp. 633-638, vol. 56, No. 5, (2002).

Bawani, M. et al., "A Single Blinded, Prospectively Randomized Comparison of Oral Phosphosoda (OP) with Polyethylene Glycol Based Solution (PG) as a Colonic Lavage for Colonoscopy," Am. J. Gastroent., p. 1350, vol. 86, Abstract 239, (1991).
Bawani, M.N. et al., "A Single Blind Control Study of Fleet Oral Phosphosoda Laxative and Magnesium Citrate for Colonoscopy Preparation," AJG, p. 1964, vol. 91, Abstract 316, (1996).
Berkelhammer, C. et al., "Low-Volume Oral Colonoscopy Bowel Preparation: Sodium Phosphate and Magnesium Citrate," Gastrointestinal Endoscopy, pp. 89-94, vol. 56, No. 1, (2002).
Bujnada, L. et al., "Tolerance and Colon Cleansing with Two Preparations. Polyethylene Glycol Versus Sodium Phosphate," Gastroenterologia Y. Hepatologia, pp. 9-12, vol. 24, (2001).
Chaleoykitti, B., "Comparative Study Between Polyethylene Glycol and Sodium Phosphate Solution in Elective Colorectal Surgery," J. Med. Assoc. Thai, pp. 92-96, vol. 85, (2002).
Chan, A. et al., "Use of Oral Sodium Phosphate Colonic Lavage Solution by Canadian Colonoscopists: Pitfalls and Complications," Can J. Gastroenterol., pp. 334-338, vol. 11, No. 4, (1997).
Chia, Y.W. et al., "Role of Oral Sodium Phosphate and its Effectiveness in Large Bowel Preparation for Out-Patient Colonoscopy," J.R. Coll. Surg. Edinb., pp. 374-376, vol. 40, (1995).
Chilton, A.P. et al., "A Blinded, Randomized Comparison of a Novel, Low-Dose, Triple Regimen with Fleet Phospho-Soda: A Study of Colon Cleanliness, Speed and Success of Colonoscopy," Endoscopy, pp. 37-41, vol. 32, No. 1, (2000).
Clarkston, W.K. et al., "Oral sodium phosphate versus sulfate-free polyethylene glycol electrolyte lavage solution in outpatient preparation for colonoscopy: a prospective comparison," Gastrointest. Endosc., pp. 42-48, vol. 43, (1996).
Cohen, S.M. et al., "Prospective, randomized, endoscopic-blinded trial comparing precolonoscopy bowel cleansing methods," Dis. Colon Rectum, pp. 689-696, vol. 37, (1994).
Da Silva, M.M. et al., "Colonoscopy preparation in children: safety, efficacy, and tolerance of high- versus low-volume cleansing methods," Journal of Pediatric Gastroenterology and Nutrition, pp. 33-37, vol. 24, (1997).
Del Piano, M. et al., "A comparison of 3 methods of preparation for colonoscopy," Minerva Gastroenterol. Dietol, pp. 89-92, vol. 39, (1993).
Fernandez, J.M.P. et al., "Characterization of the safety, effectiveness and use of oral sodium phosphate," Revista Espanola De Enferm. Digestivas, pp. 220-225, vol. 93, No. 4, (2001).
Frommer, D. "Cleansing ability and tolerance of three bowel preparation for colonoscopy," Dis. Colon Rectum, pp. 100-104, vol. 40, (1997).
Golub, R.W. et al., "Colonoscopic Bowel Preparations—Which One?," Dis. Colon. Rectum., pp. 594-599, vol. 38, (1995).
Greenleaf, J.E. et al., "Plasma volume expansion with oral fluids in hypohydrated men at rest and during exercise," Aviat Space Environ. Med., pp. 837-844, vol. 69, (1998).
Gremse, D.A. et al., "Comparison of oral sodium phosphate to polyethylene glycol-based solution for bowel preparation for colonoscopy in children," J. Ped. Gast. And Nutrition, pp. 586-590, vol. 23, (1996).
Habr-Gama, A., "Bowel preparation for colonoscopy: comparison of mannitol and sodium phosphate: results of a prospective randomized study," Rev. Hosp. Clin. Fac. Med. S. Paulo, pp. 187-192, vol. 54, No. 6, (1999).
Handelsman, J.C. et al., "Experience with ambulatory preoperative bowel preparation at the Johns Hopkins hospital," Arch. Surg., pp. 441-444, vol. 128, (1993).
Haroon, et al., "A randomized clinical trial comparing oral sodium phosphate (NaP) with standard polyethylene glycol-based lavage solution (Colyte) in the preparation of patients for colonoscopy," Gastroenterology, vol. 102, No. 4, Abstract No. 2112, (1992).
Henderson, J.M. et al., "Single-day, divided-dose oral sodium phosphate laxative versus intestinal lavage as preparation for colonoscopy: efficacy and patient tolerance," Gastrointest. Endoscopy, pp. 238-243, vol. 42, No. 3, (1995).
Hookey, L.C. et al., "The safety profile of oral sodium phosphate for colonic cleansing before colonoscopy in adults", Gastrointest. Endoscopy, vol. 56, No. 6, pp. 895-902, (2002).

Huynh, T. et al., "Safety profile of 5-h oral sodium phosphate regimen for colonoscopy cleansing: lack of clinically significant hypocalcemia or hypovolemia," Am. J. Gastroenterol., pp. 104-107, vol. 90, (1995).

Johnson, D.R. et al., "Dehydration and orthostatic vital signs in women with hyperemesis gravidarum" Acad. Emerg. Med., pp. 692-697, (7 pages including correction), vol. 2, (1995).

Kim, M. et al., "Patient compliance and satisfaction with oral bowel preparation for outpatient colonoscopy: a prospective, randomized, blinded trial," Dis. Colon Rectum, vol. 40, pp. A42, Abstract No. P48, (1997).

Klein, S. et al., "Enteral and parenteral nutrition," Sleisenger and Fordtran's Gastrointestinal and Liver Disease, pp. 254-277, (1998).

Kolts, B.E. et al., "A comparison of the effectiveness and patient tolerance of oral sodium phosphate, castor oil, and standard electrolyte lavage for colonoscopy or sigmoidoscopy preparation," Am. J. Gastroenterol., pp. 1218-1223, vol. 88, No. 8, (1993).

Kuchel, G.A. et al., "Cardiovascular responses to phlebotomy and sitting in middle-aged and elderly subjects," Arch. Int. Med., pp. 366-370, vol. 152, (1992).

Lapalus, M-G. et al., "Prospective randomized single-blind trial comparing oral sodium phosphate and polyethylene glycol based solution for colonoscopy preparation," Gastroenterol. Clin. Biol., pp. 29-34, vol. 25, (2001).

Lee, J. et al., "A prospective randomised study comparing polyethylene glycol and sodium phosphate bowel cleansing solutions for colonoscopy," The Ulster Medical Journal, pp. 68-72, vol. 68, No. 2, (1999).

McGee, S.R., "Physical examination of venous pressure: a critical review," Am. Heart J., pp. 10-18, vol. 136, (1998).

Macari, M. et al., "Effect of different bowel preparations on residual fluid at CT colonography," Radiology, pp. 274-277, vol. 218, (2001).

Macleod, A.J.M. et al., "A comparison of fleet phospho-soda with picolax in the preparation of the colon for double contrast barium enema," Clinical Radiology, pp. 612-614, vol. 53, (1998).

Marshall, J.B. et al., "Short report: prospective, randomized trial comparing a single dose sodium phosphate regimen with PEG-electrolyte lavage for colonoscopy preparation," Aliment Pharmacol. Ther., pp. 679-682, vol. 7, (1993).

Marshall, J.B. et al., "Prospective, randomized trial comparing sodium phosphate solution with polyethylene glycol-electrolyte lavage for colonoscopy preparation," Gastrointest. Endosc., pp. 631-634, vol. 39, No. 5, (1993).

Martinek, J. et al., "Cisapride does not improve precolonoscopy bowel preparation with either sodium phosphate or polyethylene glycol electrolyte lavage," Gastrointest. Endoscopy, pp. 180-185, vol. 54, No. 2, (2001).

Maughan, R.J. et al., "Post-exercise rehydration in man: effects of electrolyte addition to ingested fluids," Eur. J. Appl. Physiol. Occup. Physiol., pp. 209-215, vol. 69, (1994).

O'Donovan, A.N. et al., "A prospective blinded randomized trial comparing oral sodium phosphate and polyethylene glycol solutions for bowel preparation prior to barium enema," Clin. Radiology, pp. 791-793, vol. 52, (1997).

Oliveria, L.C.C. et al., "Mechanical bowel preparation for elective colorectal surgery; a prospective, randomized, surgeon-blinded trial comparing sodium phosphate and polyethylene glycol-based oral lavage solutions," Dis. Colon Rectum, pp. 585-591, vol. 40, (1997).

Poon, C.M. et al., "Two liters of polyethylene glycol-electrolyte lavage solution versus sodium phosphate as bowel cleansing regimen for colonoscopy: a prospective randomized controlled trial," Endoscopy, pp. 560-563, vol. 34, (2002).

Rex, D.K. et al., "Impact of bowel preparation on efficacy and cost of colonoscopy," Am. J. Gastroenterology, pp. 1696-1700, vol. 97, No. 7, (2002).

Shaoul, R. et al., "Symptoms of hyperphosphatemia, hypocalcemia, and hypomagnesemia in an adolescent after the oral administration of sodium phosphate in preparation for a colonoscopy," Gastrointest. Endosc., pp. 650-652, vol. 53, No. 6, (2001).

Sudduth, R.H. et al., "The effectiveness of simethicone in improving visibility during colonoscopy when given with a sodium phosphate solution: a double-blind randomized study," Gastrointest. Endoscopy, pp. 413-415, vol. 42, No. 5, (1995).

Thomson, A. et al., "Bowel preparation for colonoscopy: a randomized prospective trial comparing sodium phosphate and polyethylene glycol in a predominantly elderly population," J. Gast. and Hepatology, pp. 103-107, vol. 11, (1996).

Unal, S. et al., "A randomized prospective trial comparing 45 and 90-ml oral sodium phosphate with X-Prep in the preparation of patients for colonoscopy," Acta. Gastro-Enterol. Belg., pp. 281-284, vol. 61, (1998).

Wolff, B.G. et al., "A new bowel preparation for elective colon and rectal surgery: a prospective, randomized clinical trial," Arch. Surg., pp. 895-900, vol. 123, (1998).

Yoshioka, K. et al., "Randomized trial of oral sodium phosphate (picolax) for elective colorectal surgery and colonoscopy," Dig. Surg., pp. 66-70, vol. 17, (2000).

Young, C.J. et al., "Oral sodium phosphate solution is a superior colonoscopy preparation to polyethylene glycol with bisacodyl," Dis. Colon Rectum, pp. 1568-1571, vol. 43, (2000).

Tjandra, J. et al., "Carbohydrate-Electrolyte (E-Lyte®) Solution Enhances Bowel Preparation With Oral Fleet® Phospho-soda®", Dis Colon Rectum, 47, pp. 1181-1186, (2004).

Canard, J. et al., "Fleet® Phospho Soda: for Greater Acceptability of the Colic Preparation Before Colonoscopy. Randomized Comparative Single Blind Study Versus Polyethylene Glycol." Acta. Endoscopica, pp. 703-708, vol. 31, (2001).

Translation of the Canard, J., et al reference. English Language Translation of document "X123" (above), no date indicated for translation.

Oliveira, L. et al., "Mechanical Bowel Preparation With Oral Sodium Phosphate Solution for Colonoscopy. A New Small Volume Solution Compared to the Traditional Mannitol.", Revista do Colegio Brasileiro de Cirurgioes, pp. 353-358, vol. 26, (1999).

Translation of the Oliveira, L. et al reference. English Language Translation of document "X125" (above), no date indicated for translation.

Salix Pharmaceuticals, Inc., Visicol® Tablets Product Information, 2 pages, (2005).

Isbrucker, R.A. et al., "Risk and safety assessment on the consumption of licorice root (*Glycyrrhiza* sp.), its extract and powder as a food ingredient, with emphasis on the pharmacology and toxicology of glycyrrhizin", Regulatory Toxicology and Pharmacology, vol. 46, pp. 167-192, (2006).

Translation of the Belgium Patent BE 541665 dated Aug. 1959.

Unger et al., "Willingness to Undergo Split-Dose Bowel Preparation for Colonoscopy and Compliance with Split-Dose Instructions," Dig Dis Sci, pp. 2030-2034, (2010).

International Search Report dated Dec. 4, 2008 for PCT Application No. PCT/US08/073855.

Gimenez, L., et al., "Prevention of phosphate-induced progression of uremia in rats by 3-phosphocitric acid", Kidney International, vol. 22, pp. 36-41, (1982).

Zechner, V. O., et al., "The Conservative treatment of phosphate calculi with citrate buffer", Wiener Klinische Wochenschrift, vol. 87, No. 9, pp. 300-303, (1975).

Abuelo, J.G. "Normotensive ischemic acute renal failure", New England Journal of Medicine, vol. 357, pp. 797-805, (2007).

* cited by examiner

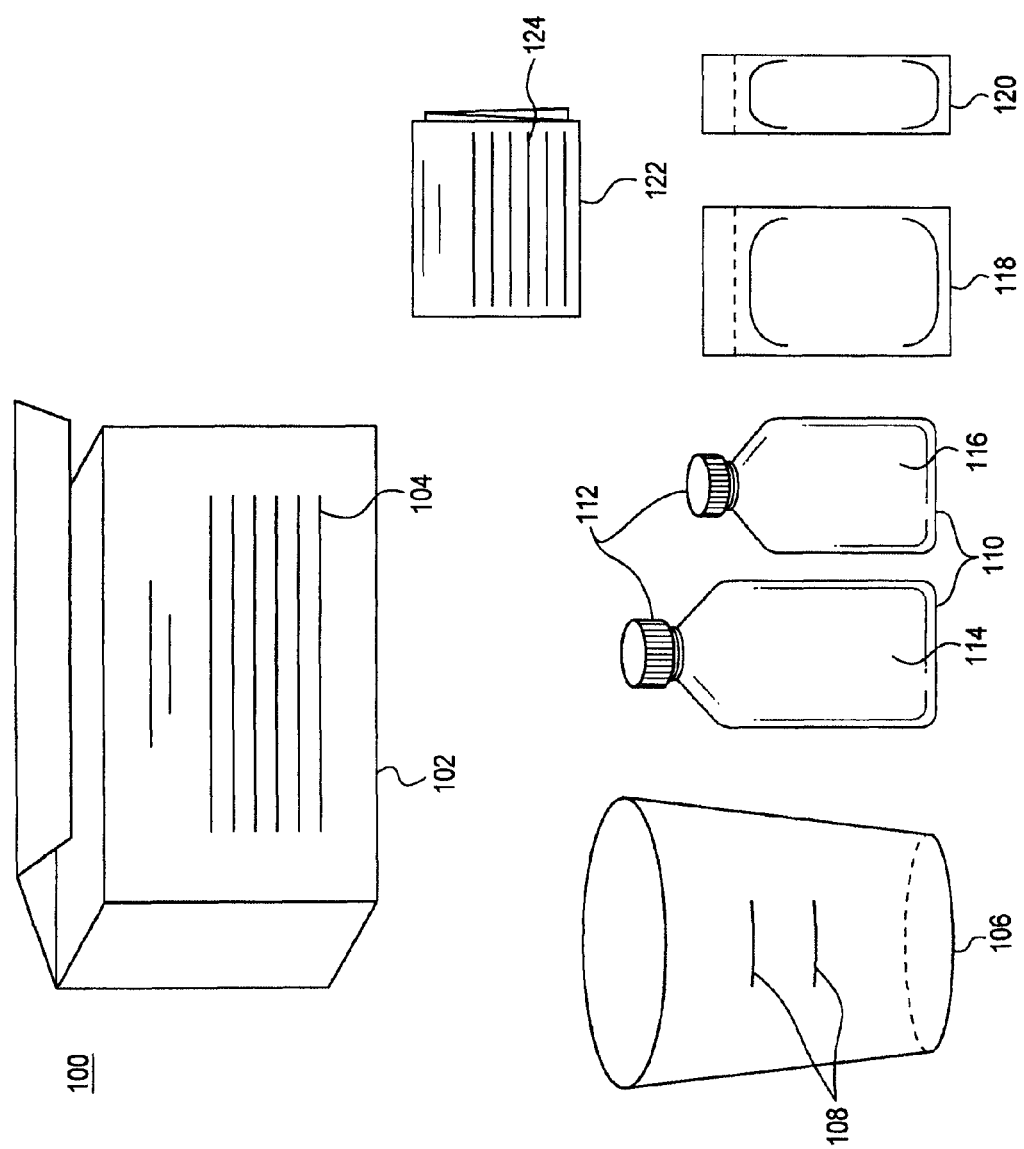

LOW DOSE COLONIC CLEANSING SYSTEM

REFERENCE TO RELATED APPLICATIONS

This application is a divisional application of allowed U.S. application Ser. No. 11/839,474, filed Aug. 15, 2007 now U.S. Pat. No. 7,998,510, entitled "Low Dose Colonic Cleansing System", which claims the benefit of U.S. Provisional Application No. 60/822,703 entitled "Low Dose Colonic Cleansing System" filed Aug. 17, 2006, the entire contents of which are hereby incorporated by reference in its entirety.

BACKGROUND

Aqueous solutions of sodium phosphate salts (monobasic and dibasic sodium phosphate), such as FLEET® PHOSPHO-SODA®, are very effective oral cathartics and are extensively used prior to colonoscopy, radiographic procedures, and surgery. For pre-colonoscopy use, a split regimen is preferred that includes one 45 mL dose given the evening before colonoscopy and a second 45 mL dose given at least three hours prior to the procedure on the following morning. Each 45 mL dose contains 21.6 g monobasic sodium phosphate, and 8.1 g dibasic sodium phosphate. Patients are instructed to consume only a clear liquids diet for the meal proceeding the first dose, and to drink large amounts of clear liquids, including water and oral rehydration solutions, for example 3 to 4 liters, after each dose. See, for example, US Published Patent Application publication no. US20040192614 to Vanner et al.

SUMMARY

In a first aspect, the invention is a method of colonic cleansing, comprising administering orally a first dose of a liquid osmotic colonic evacuant composition; and administering orally a second dose of the liquid osmotic colonic evacuant composition. The second dose comprises an amount of the liquid osmotic colonic evacuant composition that is 55% to 95% of the amount of the first dose of the liquid osmotic colonic evacuant composition.

In a second aspect, the invention is a kit for colonic cleansing, comprising a first dose of an osmotic colonic evacuant composition; and a second dose of the osmotic colonic evacuant composition. The second dose comprises an amount of the osmotic colonic evacuant composition that is 55% to 95% of the amount of the first dose of the osmotic colonic evacuant composition. The osmotic colonic evacuant is not in the form of tablets or capsules.

In a third aspect, the invention is a kit for colonic cleansing, comprising an osmotic colonic evacuant composition; and at least one dosage container. The at least one dosage container has markings to denote a first dose and a second dose, and the second dose comprises an amount that is 55% to 95% of the amount of the first dose.

In a fourth aspect, the invention is a method of colonic cleansing with a low dose colonic cleansing system, comprising administering orally 45 mL of an osmotic colonic evacuant composition; and administering orally 30 mL of the osmotic colonic evacuant composition. The low dose colonic cleansing system comprises 0.45 gram/mL of monobasic sodium phosphate and 0.18 gram/mL of dibasic sodium phosphate when solubilized in water, at least one packet comprising a flavorant, and at least one dosage container.

BRIEF DESCRIPTION OF THE DRAWINGS

FIG. 1 depicts components of the kit for one preferred embodiment of the low-dose colonic cleansing system.

DETAILED DESCRIPTION

Because a hypertonic solution of sodium phosphate salts acts as an osmotic colonic evacuant of limited duration, it was previously thought that the administration of two equivalent doses of the salt cathartic solution was necessary to promote effective colonic cleansing. The present invention is drawn to the unexpected and surprising finding of effective phosphate salt-based colonic cleansing systems that employ a second dosage amount smaller than required previously.

The present invention makes use of the discovery of effective colonic cleansing systems when administered in dosages lower than that required in the past. In particular, the present invention makes use of the unexpected and surprising finding that colonic cleansing can be accomplished that is sufficient for colonoscopy by using a smaller dose colonic cleansing system that includes two doses of an osmotic colonic evacuant, where the second dose is reduced. Thus, the invention described herein achieves effective colonic cleansing using a smaller dose of osmotic colonic evacuant than previous colonic cleansing systems.

The phrase "osmotic colonic evacuant," as used herein, refers to any composition that induces water infusion and retention into the intestinal lumen when the composition is administered to a subject. Compositions of an osmotic colonic evacuant include solids, powders, gels, or liquids. A liquid composition of an osmotic colonic evacuant may be constituted from a solid, powder, or gel composition using a physiologically acceptable carrier (e.g., water). A liquid composition of an osmotic colonic evacuant suitable for administration also may be constituted from liquid concentrate form using a physiologically acceptable carrier (e.g., water) as diluent.

The term "cathartic," as used herein, refers to any composition that acts as a colonic evacuant for cleaning the bowels effective for colonoscopy.

The chemical composition of an osmotic colonic evacuant may be a phosphate-based cathartic, for example, sodium dihydrogen phosphate, disodium hydrogen phosphate, sodium biphosphate, sodium acid pyrophosphate, or mixtures thereof; or a sulfate-based cathartic, for example, sodium picosulfate and sodium sulfate, or mixtures thereof; or magnesium-based cathartic, for example, magnesium citrate, magnesium hydroxide, magnesium sulfate, magnesium oxide, or mixtures thereof; or magnesium sulfate (Epsom salts). Preferred osmotic colonic evacuants include magnesium sulfate or a mixture of sodium dihydrogen phosphate and disodium hydrogen phosphate. In one embodiment, the preferred osmotic colonic evacuant is the commercially available phosphate salt cathartic FLEET® PHOSPHO-SODA® (C.B. Fleet, Lynchburg, Va.; National Formulary Monograph USP 23/NF18, p. 1430), which includes sodium dihydrogen phosphate, monohydrate ($NaH_2PO_4 \cdot H_2O$) (monobasic sodium phosphate) and disodium hydrogen phosphate, heptahydrate ($Na_2HPO_4 \cdot 7H_2O$) (dibasic sodium phosphate) in water. A 45 mL dose contains 21.6 g monobasic sodium phosphate, and 8.1 g dibasic sodium phosphate.

As the first dose of the two dose treatment, preferably 15 to 25 g monobasic sodium phosphate is orally administered, for example 20 to 23 g monobasic sodium phosphate, including 21.6 g. The first dose also preferably contains 5.5 to 9.4 g dibasic sodium phosphate, for example 7.5 to 8.6 g dibasic sodium phosphate, including 8.1 g dibasic sodium phosphate.

As the second dose of the two dose treatment, preferably 55 to 95% of the first dose is orally administered, and is always less than the first dose. For example, 60 to 90% of the first dose may be used, including 60 to 70 or 80% of the first dose, such as 66%. For example, if the first dose is (i) 15 g, (ii) 20 g, (iii) 21.6 g, (iv) 23 g or (v) 25 g monobasic sodium phosphate, then the second dose could correspond to the following amounts of monobasic sodium phosphate: (i) 8.25 g to 14.25 g, including 9.0 g, 9.9 g, 10.5 g, 12.0 g and 13.5 g; (ii) 11.0 g to 19.0 g, including 12.0 g, 13.2 g, 14.0 g, 16.0 g and 18.0 g; (iii) 11.88 g to 20.52 g, including 12.96 g, 14.26 g, 15.12 g, 17.28 g and 19.44 g; (iv) 12.65 g to 21.85 g, including 13.8 g, 15.18 g, 16.1 g, 18.4 g and 20.7 g; or (v) 13.75 g to 23.75 g, including 15.0 g, 16.5 g, 17.5 g, 20.0 g, and 22.5 g. Also as an example, if the first dose contains (i) 5.5 g, (ii) 7.5 g, (iii) 8.1 g, (iv) 8.6 g or (v) 9.4 g dibasic sodium phosphate, then the second dose could correspond to the following amounts of dibasic sodium phosphate: (i) 3.02 g to 5.22 g, including 3.3 g, 3.63 g, 3.85 g, 4.4 g and 4.95 g; (ii) 4.12 g to 7.12 g, including 4.5 g, 4.95 g, 5.25 g, 6.00 g and 6.75 g; (iii) 4.45 g to 7.70 g, including 4.86 g, 5.35 g, 5.67 g, 6.48 g and 7.29 g; (iv) 4.73 g to 8.17 g, including 5.16 g, 5.68 g, 6.02 g, 6.88 g and 7.74 g; or (v) 5.17 g to 8.93 g, including 5.64 g, 6.20 g, 6.58 g, 7.52 g and 8.46 g.

Preferred phosphate salt cathartics include from 0.05 to 1.5 gram/mL of monobasic sodium phosphate and from 0.02 to 0.6 gram/mL of dibasic sodium phosphate. More preferably, the osmotic colonic evacuants of the phosphate salt cathartic variety may also include from 0.25 to 1 or from 0.4 to 1 gram/mL of monobasic sodium phosphate and from 0.1 to 0.4 or from 0.13 to 0.25 gram/mL of dibasic sodium phosphate. At present, an especially preferred phosphate salt cathartic includes about 0.48 g/mL of monobasic sodium phosphate and about 0.18 g/mL of dibasic sodium phosphate. Phosphate salt cathartics that include one phosphate salt, such as dibasic sodium phosphate, also may be used. Preferred phosphate salt cathartics have a pH from about 4.4 to about 5.2 and may be produced in multiple ways, such as by combining phosphoric acid with dibasic sodium phosphate or with caustic soda. Osmotic colonic evacuants of this type are very stable, thus having a long shelf-life, and are considered to work in a mild and very effective manner.

The colonic cleansing system may include an osmotic colonic evacuant in solid or powder form that is constituted with a physiologically acceptable carrier (e.g., water) immediately prior to administration. Optionally, the physiologically acceptable carrier may be packaged with the colonic cleansing system. The consumer may provide the source of the physiologically acceptable carrier apart from the colonic cleansing system. An example of a physiologically acceptable carrier includes sterile water. The kit will include instructions that direct the consumer about the types of physiologically acceptable carrier that may be used to constitute the osmotic colonic evacuant powder in liquid form, as well as the inclusion of any additional materials (e.g., contents of any flavor packets). Preferably, the osmotic colonic evacuant is not in the form of tablets or capsules.

In another embodiment, the colonic cleansing system may include an osmotic colonic evacuant pre-dissolved in a physiologically acceptable carrier (e.g., water). The osmotic colonic evacuant may be packaged as a total dosage form or as individual unit dosage forms (for example, a first dosage and a separately packaged second dosage). In one embodiment, the osmotic colonic evacuant is packaged as a total dosage form that is subsequently dispensed as individual unit dosage forms (a first dosage and a second dosage) using one or more dosage containers that may be included in the colonic cleansing system. The dosage container may include markings on their surfaces to denote volume fill levels appropriate for consumption of a give volume or amount of the osmotic colonic evacuant. In another preferred embodiment, the osmotic colonic evacuant is packaged as individual, ready-to-use, unit dosage forms in separate sealed containers.

Prior to consumption, flavorants and/or sweeteners may be added to the osmotic colonic evacuant to increase its palatability. Optionally, the flavorant can be present in the mixture or solution that contains the osmotic colonic evacuant. Alternatively, the flavorant and sweetener can be individually packaged apart from the osmotic colonic evacuant. The flavorant may include a citrate-based component. The citrate-based component may include citric acid, salts, such as sodium or potassium citrate, derivatives of citrate, such as a citrate derivatized with ester functionality, and the like. The flavorant also may include natural and/or artificial flavorings, such as natural and/or artificial fruit flavors, to further increase the palatability of the cathartic. Preferred sweeteners include aspartame, sucralose, and acesulfame potassium, among other ingredients. Preferably, the flavorant and sweetener may be combined as a powered mixture. Examples of such combinations include the commercially available aspartame-based drink mixture, such as the CRYSTAL LIGHT® powder that is available from Kraft Foods, Northfield, Ill. (USA) or the N&A Pink Lemonade FL System Sugar FAFT523 that is available from WILD Flavors, Inc., Erlanger, Ky. (USA). Both of these powders include aspartame, citric acid, and fruit flavors that result in flavored drinks when the powder is combined with water. Examples of compositions and uses of flavorants and sweeteners in phosphate-based cathartics are described, for example, in ASPARTAME AND CITRATE FLAVORED PHOSPHATE SALT CATHARTIC, U.S. Published Patent Application publication no. US20060051428 to Ayala et al.

In one preferred embodiment, the flavorants and sweeteners are packaged separately from the osmotic colonic evacuant in the kit. Optionally, the flavorants and sweeteners can be pre-mixed with the osmotic colonic evacuant composition of the kit.

The colonic cleansing system also includes at least one dosage container. Preferably, at least one surface of the dosage container includes markings that denote the volume fill level to achieve a unit dose of the osmotic colonic evacuant when the dosage container is filled with the osmotic colonic evacuant. The dosage container includes markings that denote two different volume fill levels to achieve different unit doses of the osmotic colonic evacuant. A first volume fill level will be greater than a second volume fill level to produce a first unit dose having a given volume of liquid and a second unit dose having a lower given volume of liquid. More preferably, a first volume fill level will be greater than a second volume fill level to produce a ratio of first unit dose:second unit dose.

In an alternative embodiment, colonic cleansing system may include a first dosage container and a second dosage container. The two dosage containers may be substantially identical or different in form, shape, size, and volume. Preferably, the first dosage container differs from the second dosage container in only size and volume such that the second dosage container may be adapted to fit within the interior of the first dosage container. Preferably, at least one surface of each dosage container includes markings that denote the volume fill level to achieve a unit dose of the osmotic colonic evacuant when the dosage container is filled with the osmotic colonic evacuant. Preferably, the first dosage container includes at least one marking to denote a volume fill level corresponding to a first unit dose of the osmotic colonic evacuant and the second dosage container includes at least one marking to denote a volume fill level corresponding to a second unit dose of the osmotic colonic evacuant. Preferably, a first volume fill level will be greater than a second volume fill level to produce a first unit dose having a given volume of liquid and a second unit dose having a lower given volume of liquid. More preferably, a first volume fill level will be greater than a second volume fill level to produce a ratio of first unit dose:second unit dose.

Optionally, the dosage container includes an additional marking to denote the volume fill level for a physiologically acceptable carrier (e.g., water). Such a marking is useful to indicate the volume of a physiologically acceptable carrier to dissolve the contents of packets of flavorant and/or sweetener. A unit dose of the osmotic colonic evacuant may be added to the dosage container containing the dissolved flavorant and/or sweetener prior to administering the liquid composition. Examples of a dosage container include cups and spoons.

Optionally, the dosage container may contain writings, pictures, symbols or other information about the use of the dosage container for colonic cleansing or other uses, or other instructions.

The osmotic colonic evacuant may also be present as tablets or capsules. A first dosage unit may be present as one, two, three, four or more tablets or capsules, and the second dosage unit may be present as one, two, three, four or more tablets or capsules. The tablets or capsules may all be the same size or may be different sizes. The first dosage form and the second dosage form may be pre-measured and separately packaged, for example the tablets or capsules may be present in a first package for the first dose, and a separate package for the second dose.

Finally, the colonic cleansing system will include instructions directing the subject on the use of the contents of the system. For one preferred embodiment, the instructions will direct the subject to constitute an osmotic colonic evacuant powder, flavorant powder and sweetener powder into an appropriate volume of a physiologically acceptable carrier (e.g., water). The appropriate volume is at least sufficient to provide for a first unit dose and a second unit dose of a liquid osmotic colonic evacuant. The instructions may direct the subject to fill at least one dosage container with the constituted liquid osmotic colonic evacuant to a first volume fill level corresponding to a first unit dose and to consume the contents of the dosage container. The instructions may direct the subject to allow for a period of time to lapse, after which the subject is directed to fill the at least one dosage container with the constituted liquid osmotic colonic evacuant to a second volume fill level corresponding to a second unit dose and consume the contents of the dosage container. Preferably, the instructions would direct the subject to consume a first unit dose and a second unit dose of the constituted osmotic colonic evacuant where the ratio of first unit dose:second unit dose is greater than 1.00. Most preferably, the instructions would direct the subject to consume a 45 mL first unit dose and a 30 mL second unit dose of the constituted osmotic colonic evacuant comprising FLEET® PHOSPHO-SODA® (C.B. Fleet, Lynchburg, Va.; National Formulary Monograph USP 23/NF18, p. 1430), optionally supplemented with a flavorant and a sweetener.

The markings on the dosage container(s) are particularly advantageous for kits that contain a total dosage form because such markings facilitate the accurate dispensing of the appropriate volume of the osmotic colonic evacuant for consumption. In the case of kits containing individual dosage unit forms, the volume of each dosage form will be pre-determined by the fill capacity of each sealed container. Thus, the instructions of such kits need only direct the consumer to pour the contents of a given individual dosage unit form into the dosage container for consumption without reference to markings on the dosage container.

FIG. 1 depicts a colonic cleansing kit 100 having aspects of the present invention. The kit 100 includes an exterior package 102, one or more dosage containers 106, one or more sealed containers 110 having a sealed top 112, one or more envelope containers 118 and 120 and an instruction pamphlet 122. The exterior package 102 may be composed of paper and/or plastic components and may be imprinted with descriptive product information 104. The exterior package 102 may enclose multiple containers, such as containers 106, 114, 116, 118, and 120, one or more supporting structures for the multiple containers, usually having paper and/or plastic components, and a pamphlet 122 containing instructions for use 124, and the like. The instruction pamphlet 122 includes directions regarding how to prepare the osmotic colonic evacuant composition (e.g., FLEET® PHOSPHO-SODA® liquid with the flavorant and sweetener) and when to consume the colonic cleansing composition in relation to the time of a colonoscopy procedure. The supporting structures may be formed from stiff paper, STYROFOAM™, and the like.

The surface of one or more dosage containers 106 may have optional markings 108 to denote volume fill levels. The containers 110 may be fitted with screw-lid tops 112 to provide an air-tight seal. The sizes of containers 110 are adapted to contain a first volume 114 and a second volume 116 of an osmotic colonic evacuant. Containers 110 include the osmotic colonic evacuant. The containers 118 and 120 may include the flavorant, sweetener and the like. The surface of one or more dosage containers 106 may include writings, pictures, symbols or other information about the use of the dosage container for colonic cleansing or other uses. The containers may take the form of bottles, tubs, sachets, envelopes, tubes, ampoules, and the like, which may be formed in part or in whole from plastic, glass, paper, foil, MYLAR®, wax, and the like. The containers may be equipped with fully or partially detachable lids that may initially be part of the containers or may be affixed to the containers by mechanical, adhesive, or other means.

By orally administering the compositions of the present invention to a subject, the colon may be cleansed. A first aliquot of the composition may be administered to the subject about 14 hours prior to the colonoscopy. This initial dose is followed by a second aliquot of the composition administered about 3 hours prior to the colonoscopy. A surprising and unexpected finding of the present invention is that effective colonic cleansing suitable for colonoscopy examination can be accomplished with consumption of a lower second dose of the osmotic colonic evacuant relative to the first dose of the osmotic colonic evacuant consumed. The subject should consume large amounts of liquids, 3 to 4 Liters for example, in addition to the composition to maintain adequate hydration. These additional liquids may include aqueous solutions that include oral re-hydration salts and/or electrolytes, such as HYDRALIFE™ and other oral re-hydration beverages.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A kit for colonic cleansing, comprising:
a first dose of an osmotic colonic evacuant composition, and
a second dose of the osmotic colonic evacuant composition,
wherein the second dose comprises an amount of the osmotic colonic evacuant composition that is 60% to 70% of the amount of the first dose of the osmotic colonic evacuant composition, and
the osmotic colonic evacuant is not in the form of tablets or capsules.

2. A kit of claim 1, wherein the osmotic colonic evacuant composition comprises a phosphate cathartic.

3. The kit of claim 2, wherein the phosphate cathartic comprises monobasic sodium phosphate and dibasic sodium phosphate.

4. The kit of claim 3, wherein the first dose of the phosphate cathartic comprises from 15 to 25 g monobasic sodium phosphate and from 5.5 to 9.4 g dibasic sodium phosphate.

5. The kit of claim 3, wherein the first dose of the phosphate cathartic comprises 20 to 23 g monobasic sodium phosphate and 7.5 to 8.6 g dibasic sodium phosphate.

6. The kit of claim 3, wherein the second dose of the phosphate cathartic comprises 12.96 to 15.12 g monobasic sodium phosphate and 4.86 to 5.67 g dibasic sodium phosphate.

7. The kit of claim 3, wherein the phosphate cathartic comprises water.

8. The kit of claim 3, wherein the first dose and the second dose of the phosphate cathartic are in a single sealed container.

9. The kit of claim 3, wherein the first dose and the second dose of the phosphate cathartic are in separate sealed containers.

10. The kit of claim 3, further comprising a flavorant and a sweetener.

11. The kit of claim 3, wherein the phosphate cathartic comprises powder.

12. The kit of claim 11, wherein the first dose and the second dose of the phosphate cathartic are in a single sealed container.

13. The kit of claim 11, wherein the first dose and the second dose of the phosphate cathartic are in separate sealed containers.

14. The kit of claim 3, further comprising a dosage container.

15. A kit for colonic cleansing, comprising:
an osmotic colonic evacuant composition; and
at least one dosage container,
wherein the at least one dosage container has markings to denote a first dose and a second dose, and
the second dose comprises an amount that is 60% to 70% of the amount of the first dose.

16. The kit of claim 15, wherein osmotic colonic evacuant composition comprises a phosphate cathartic.

17. The kit of claim 15, wherein the phosphate cathartic comprises monobasic sodium phosphate and dibasic sodium phosphate.

18. A kit for colonic cleansing, comprising:
a first sealed container filled with 45 mL of an osmotic colonic evacuant composition;
a second sealed container filled with 30 mL of the osmotic colonic evacuant composition;
at least one packet comprising a flavorant; and
at least one dosage container;
wherein the osmotic colonic evacuant composition comprises 0.45 gram/mL of monobasic sodium phosphate and 0.18 gram/mL of dibasic sodium phosphate and
the at least one dosage container has at least one marking to denote a volume fill level.

* * * * *